US005993371A

United States Patent [19]

White et al.

[11] Patent Number: 5,993,371

[45] Date of Patent: Nov. 30, 1999

[54] TRANSPARENT SOAP BARS CONTAINING ALKYL POLYGLYCOSIDES

[75] Inventors: J. Matthew White, Morrow, Ohio; Donald V. Kinsman, Ft. Thomas, Ky.

[73] Assignee: Henkel Corporation, Gulph Mills, Pa.

[21] Appl. No.: 08/764,477

[22] Filed: Dec. 12, 1996

Related U.S. Application Data

[60] Provisional application No. 60/010,280, Jan. 22, 1996.

[51] Int. Cl.[6] ........ A61K 7/50

[52] U.S. Cl. ........ 511/147; 510/151; 510/152; 510/155

[58] Field of Search ........ 510/130, 137, 510/147, 151, 152, 153, 155

[56] References Cited

U.S. PATENT DOCUMENTS

| | | | |
|---|---|---|---|
| 2,820,768 | 1/1958 | Fromont | 252/118 |
| 3,562,167 | 2/1971 | Kamen et al. | 252/121 |
| 3,793,214 | 2/1974 | O'Neill et al. | 252/117 |
| 3,926,828 | 12/1975 | O'Neil et al. | 252/117 |
| 3,951,842 | 4/1976 | Prince et al. | 252/117 |
| 3,969,259 | 7/1976 | Lages | 252/107 |
| 4,165,293 | 8/1979 | Gordon | 252/118 |
| 4,206,069 | 6/1980 | Bordello | 252/122 |
| 4,297,230 | 10/1981 | Rasser | 252/117 |
| 4,396,521 | 8/1983 | Borrello | 252/118 |
| 4,397,760 | 8/1983 | Story et al. | 252/370 |
| 4,468,338 | 8/1984 | Lindberg | 252/105 |
| 4,474,683 | 10/1984 | Story et al. | 252/369 |
| 4,493,786 | 1/1985 | Joshi | 252/368 |
| 4,504,433 | 3/1985 | Imui et al. | 264/232 |
| 4,517,107 | 5/1985 | Clarke et al. | 252/108 |
| 4,695,395 | 9/1987 | Caswell et al. | 252/121 |
| 4,963,284 | 10/1990 | Novakovic et al. | 252/108 |
| 5,264,144 | 11/1993 | Moroney et al. | 252/117 |
| 5,264,145 | 11/1993 | French et al. | 252/117 |
| 5,266,690 | 11/1993 | McCurry, Jr. et al. | 536/18.6 |
| 5,310,495 | 5/1994 | Hill et al. | 252/118 |
| 5,340,492 | 8/1994 | Kacher et al. | 252/112 |
| 5,417,876 | 5/1995 | Tokosh et al. | 252/108 |
| 5,496,489 | 3/1996 | Dussault et al. | 252/134 |
| 5,529,714 | 6/1996 | Tokosh | 252/108 |

FOREIGN PATENT DOCUMENTS

| | | |
|---|---|---|
| 58-208393 | 12/1983 | Japan . |
| 61-293300 | 12/1986 | Japan . |

OTHER PUBLICATIONS

"Transparent Soap Bars—Past and Present", Soap & Chemical Specialties, Oct., 1967, pp. 102, 104, 106, 114, 115.

Dr. J. Lee Phelps, "Glycerine Bar Soap", Cosmetics & Toiletries, Allured Publishing Corp., vol. 102, Nov., 1987, pp. 49–52.

*Primary Examiner*—Necholus Ogden

*Attorney, Agent, or Firm*—Wayne C. Jaeschke; John E. Drach; Steven J. Trzaska

[57] ABSTRACT

Transparent soap bars having improved lathering and foaming characteristics contain (1) an alkanolamine; (2) an alkyl polyglycoside of the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6: (3) a polyol; (4) a fatty acid which is at least 70% neutralized by sodium hydroxide, and; (5) water wherein the water to free alkanolamine weight ratio is greater than 1.0 and the ratio of the weight of the polyol to the sum of the weights of free alkanolamine+alkyl polyglycoside+polyol+water is less than about 0.4.

52 Claims, 2 Drawing Sheets

TRANSPARENT SOAP BARS CONTAINING ALKYL POLYGLYCOSIDES

BENEFIT OF EARLIER FILING DATE UNDER 37 CFR 1.78(a)(4)

This application claims the benefit of earlier filed and copending provisional application Ser. No. 60/010,280, filed on Jan. 22, 1996.

BACKGROUND OF THE INVENTION

1. Field of the Invention

This invention relates to transparent soap bars. More specifically, the present invention relates to transparent soap bars which exhibit improved lathering and foaming characteristics due to the presence of alkyl polyglycosides.

2. Description of the Related Art

Transparent soap bars are normally milder than opaque bars. These soaps depend for their distinctive appearance upon the fact that soap is deposited from alcoholic solution in a transparent, ultramicrocrystalline form. The incorporation of glycerol and sugars also tend to cause soap to assume this form. The effect is entirely physical, and depends upon the conditions under which the soap crystallizes rather than the presence of alcohol or any other substance in the finished soap cake. Thus, a transparent soap made with the aid of alcohol retains its appearance after most of the alcohol has been evaporated from it.

Transparent soaps vary greatly in composition. They may be prepared simply by dissolving soap flakes in alcohol and then driving off the greater part of the alcohol. Such a product will not be greatly different in composition from the original soap flakes. A more usual method of manufacture, however, is to add alcohol and glycerol, in the proportion of about two parts of alcohol to one of glycerol, to a hot saponified batch of semi-boiled soap until a rapidly cooled sample is clear, after which the batch is framed in the usual way. Sugar may also be added. The fats used in transparent soaps usually are tallow and coconut oil. Up to about 30% castor oil is often used in the fat charge, as the presence of this oil reduces the amount of alcohol, glycerol or sugar required to render the soap transparent. The anhydrous soap content of transparent soaps is usually well under 50%.

There has always been a need to increase the lathering and foaming characteristics of transparent soap bars by inclusion of various types of surfactants. However, it has been found that when a synthetic surfactant is added to a transparent soap formulation, the resulting bar is not transparent. It is, therefore, an object of the present invention to increase the lathering and foaming characteristics of transparent soap bars without causing a reduction in the transparency of the bar.

SUMMARY OF THE INVENTION

One aspect of the present invention is the surprising discovery that soap bars having improved lathering and foaming characteristics with no concomitant loss in transparency can be made by incorporating alkyl polyglycosides into the bars. It has been further discovered that in order to incorporate the alkyl polyglycosides the relative amounts of the components must lie within defined ranges. The soap bars according to the invention are comprised of: (1) an alkanolamine; (2) an alkyl polyglycoside of the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6: (3) a polyol; (4) a fatty acid which is at least 70% neutralized by sodium hydroxide, and; (5) water wherein the water to free alkanolamine weight ratio is greater than 1.0 and the ratio of the weight of the polyol to the sum of the weights of free alkanolamine+alkyl polyglycoside+polyol+water is less than about 0.4. The bars contain a greater amount of water than previously known transparent bars which also contain an alkanolamine such as triethanolamine. Transparent personal cleansing bars with low triethanolamine level are more stable during the processing of the soap. Transparent bars with reduced amounts of triethanolamine exhibit better color and are less odoriferous than bars with higher levels of triethanolamine.

Another aspect of the present is the surprising discovery that transparent soap bars having improved lathering and foaming characteristics can be made by incorporating a dicarboxylic acid, such as a dimer acid, and/or a salt of a dicarboxylic acid into the fatty acid component to inhibit the formation of hazy domains in a transparent soap bar.

Yet another aspect of the present invention is the surprising discovery that transparent soap bars having improved lathering and foaming characteristics can be made by incorporating a branched fatty acid alone or in combination with a dicarboxylic acid and/or a salt of a dicarboxylic acid to inhibit the formation of hazy domains in a transparent soap bar.

Still another aspect of the present is the surprising discovery that the addition of a relatively small amount of an additive which is comprised of the product of the reaction of a monocarboxylic acid, a dicarboxylic acid, and a polyol also inhibits the formation of hazy domains in a transparent soap bar.

DESCRIPTION OF THE PREFERRED EMBODIMENTS

Figure 1:
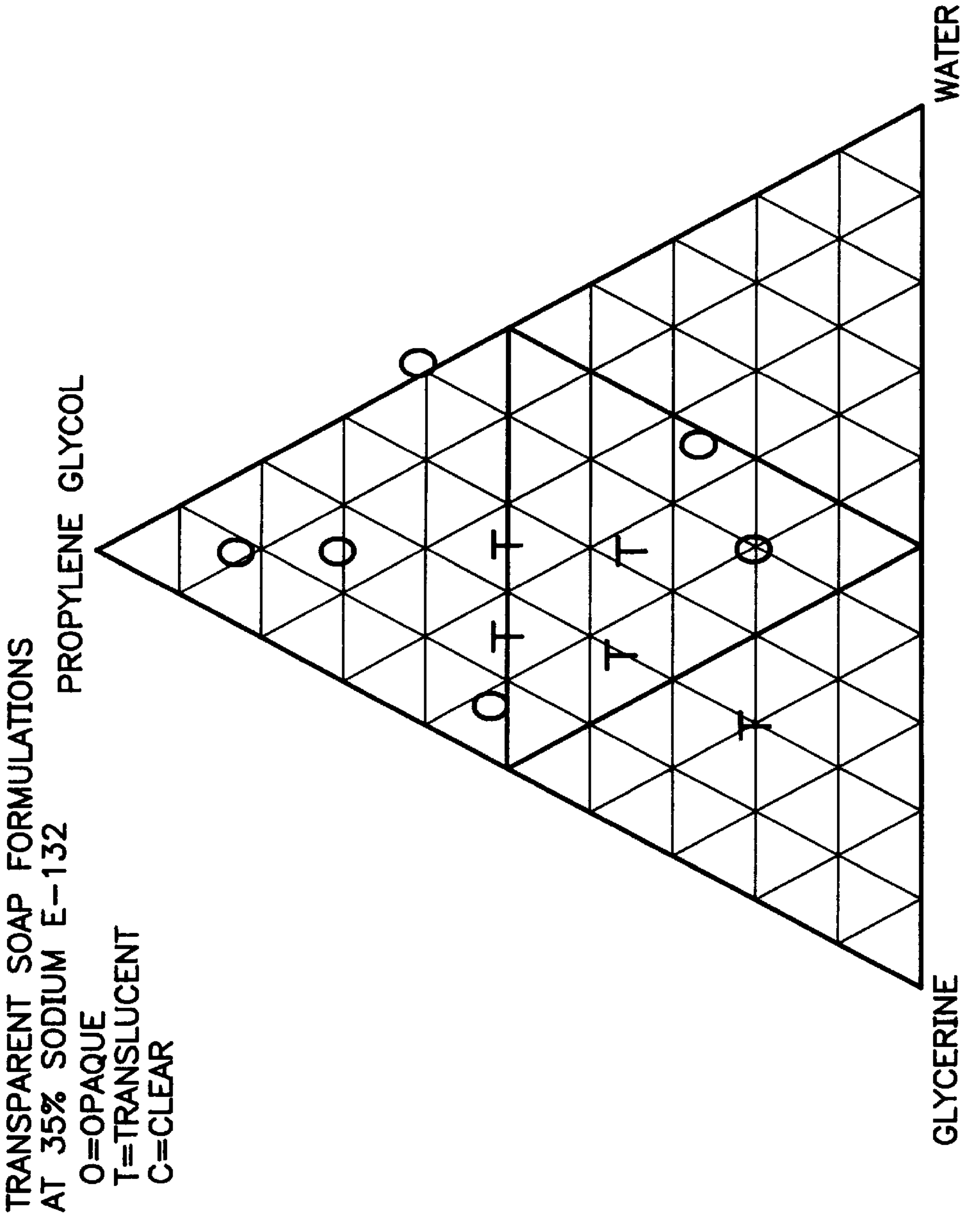
FIG. 1 is a representative three component phase diagram for a transparent soap bar which shows the transparent region for a relative amounts of water, 1,2-propylene glycol and glycerine.

Other than in the claims and in the operating examples, or where otherwise indicated, all numbers expressing quantities of ingredients or reaction conditions used herein are to be understood as modified in all instances by the term "about".

For purposes of this invention, a soap bar is deemed to be transparent when 12 pt type is readable through an one inch thick bar. A bar is deemed to be translucent when 3 mm wide printing is readable through an one inch thick bar. Also for purposes of this invention, "free" alkanolamine refers to any molar excess alkanolamine beyond that which is required for neutralization of any acid present in the bar composition.

The transparent soap bars according to the invention are comprised of: (1) an alkanolamine; (2) an alkyl polyglycoside of the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6: (3) a polyol; (4) a fatty acid which is at least 70% neutralized by sodium hydroxide, and; (5) water wherein the water to free alkanolamine weight ratio is greater than 1.0 and the ratio of the weight of the polyol to the sum of the weights of free alkanolamine+alkyl polyglycoside+polyol+water is less than about 0.4.

The alkanolamine component of the soap bars according to the invention can be any of the commonly known alkanolamines. Such alkanolamines include, but are not limited to, monoethanolamine, diethanolamine, triethanolamine, monoisopropanolamine, diisopropanolamine, triisopropanolamine, mono-sec-butanolamine, di-sec-butanolamine, tri-sec-butanolamine, 2-amino-2-methyl-1-propanol, 2-amino-2-ethyl-1,3-propanediol, tris (hydroxymethyl)aminomethane, 2-amino-2-(hydroxymethyl)-1,3-propanediol. Preferred alkanolamines are monoethanolamine, diethanolamine, and triethanolamine. Triethanolamine is most preferred. The amount of alkanolamine that can be used can be from 7 to 25 wgt. %, preferably from 21 to about 48 wgt. % as long as the water/free alkanolamine ratio is greater than 1.0.

The alkyl polyglycosides which can be used in the compositions according to the invention have the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and having an average degree of polymerization of 1.7.

2. APG® 425 Surfactant—an alkyl polyglycoside in which the alkyl group contains 8 to 16 carbon atoms and having an average degree of polymerization of 1.6.

3. APG® 625 Surfactant—an alkyl polyglycoside in which the alkyl groups contains 12 to 16 carbon atoms and having an average degree of polymerization of 1.6.

4. APG® 325 Surfactant—an alkyl polyglycoside in which the alkyl groups contains 9 to 11 carbon atoms and having an average degree of polymerization of 1.6.

5. GLUCOPON® 600 Surfactant—an alkyl polyglycoside in which the alkyl groups contains 12 to 16 carbon atoms and having an average degree of polymerization of 1.4.

6. PLANTAREN® 2000 Surfactant—a $C_{8-16}$ alkyl polyglycoside in which the alkyl group contains 8 to 16 carbon atoms and having an average degree of polymerization of 1.4.

7. PLANTAREN® 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkyl polyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated. The inclusion of alkyl polyglycosides into transparent soap bar formulations containing alkanolamines, polyols, water, and alkali soaps inhibits weeping of water and poyols. A preferred alkyl polyglycoside is one which has an average degree of polymerization of 1.7 and wherein the alkyl group contains 8 to 10 carbon atoms. Another preferred alkyl polyglycoside is one which has an average degree of polymerization of 1.6 and wherein the alkyl group contains 12 to 16 carbon atoms. The amount of alkyl polyglycoside that can be used can be from 0.5 to 40 wgt. % and preferably from 10–16 wgt. %.

The polyol component of the soap bars according to the invention can be any aliphatic compound having 2 or more alcohol functionalities. Such polyols include diols, triols, tetraols, etc. Examples of such polyols include, but are not limited to, ethylene glycol, 1,2-propylene glycol, 1,3-propylene glycol, diethylene glycol, dipropylene glycol, triethylene glycol, 1,6-hexylene glycol, glycerine, polyglycerols, monosaccharides such as glucose or fructose, disaccharides such as sucrose, sorbitol, and polyvinyl alcohol. Preferred polyols include 1,2-propylene glycol, glycerine, polyglycerol, and sorbitol. The most preferred polyol is glycerine. The amount of polyol that can be used must be greater than 1.5 wgt. %.

The fatty acid component of the soap bars according to the invention can be any saturated or unsaturated, branched or linear carboxylic acid having from 8 to 30 carbon atoms or a mixture of such acids. In a preferred embodiment of the soap bars according to the invention, the fatty acid component is a mixture of fatty acids comprised of 60% by weight of a typical commercial grade stearic acid and 40% by weight of a typical commercial grade partially hydrogenated coconut fatty acid. An example of a typical commercial grade stearic acid is EMERSOL® 132 Stearic Acid, a trademark product of Henkel Corporation, Emery Group, Cincinnati, Ohio, which has an average weight percent composition of 2.5% myristic acid, 1% pentadecanoic acid, 50% palmitic acid, 1.5% margaric acid, and 45.5% stearic acid. An example of a typical commercial grade partially hydrogenated coconut fatty acid is EMERY® 625 Partially Hydrogenated Coconut Fatty Acid, a trademark product of Henkel Corporation, Emery Group, Cincinnati, Ohio, which has an average weight percent composition of 49% lauric acid, 19% myristic acid, 9% palmitic acid, 7% stearic acid, 7% caprylic acid, 6% capric acid, and 3% oleic acid. Preferably, such a fatty acid is at least 70% neutralized by sodium hydroxide. The amount of fatty acid component that can be used in the soap bars according to the invention can range from 20 to 60 wgt. % and preferably from 30 to 55 wgt. %.

The preferred degree of neutralization of the fatty acids can range from 70% to 110% with the most preferred range being 85–95%. The fatty acids can be neutralized by bases such as alkali metal hydroxides such sodium hydroxide to up to 100% neutralization or potassium hydroxide to up to 20% neutralization. An additional degree of neutralization can be accomplished by the alkanolamine component. The total amount of all types of carboxylic acid, including the fatty acid which is part of the transparent soap bar formulation and any added dicarboxylic acid and/or branched acid can be from 18 to 60 wgt. % and preferably from 23 to 38 wgt. %.

The amount of water that can used in the soap bars according to the invention is expressed as the water/free alkanolamine ratio and must be greater than 1.0. The relative amount of polyol can be expressed as a fraction equal to the weight of polyol/the total of the weights of free alkanolamine+polyol+water+alkyl polyglycoside. The value of the fraction can range from 0.1 to 0.4.

Figure 2:
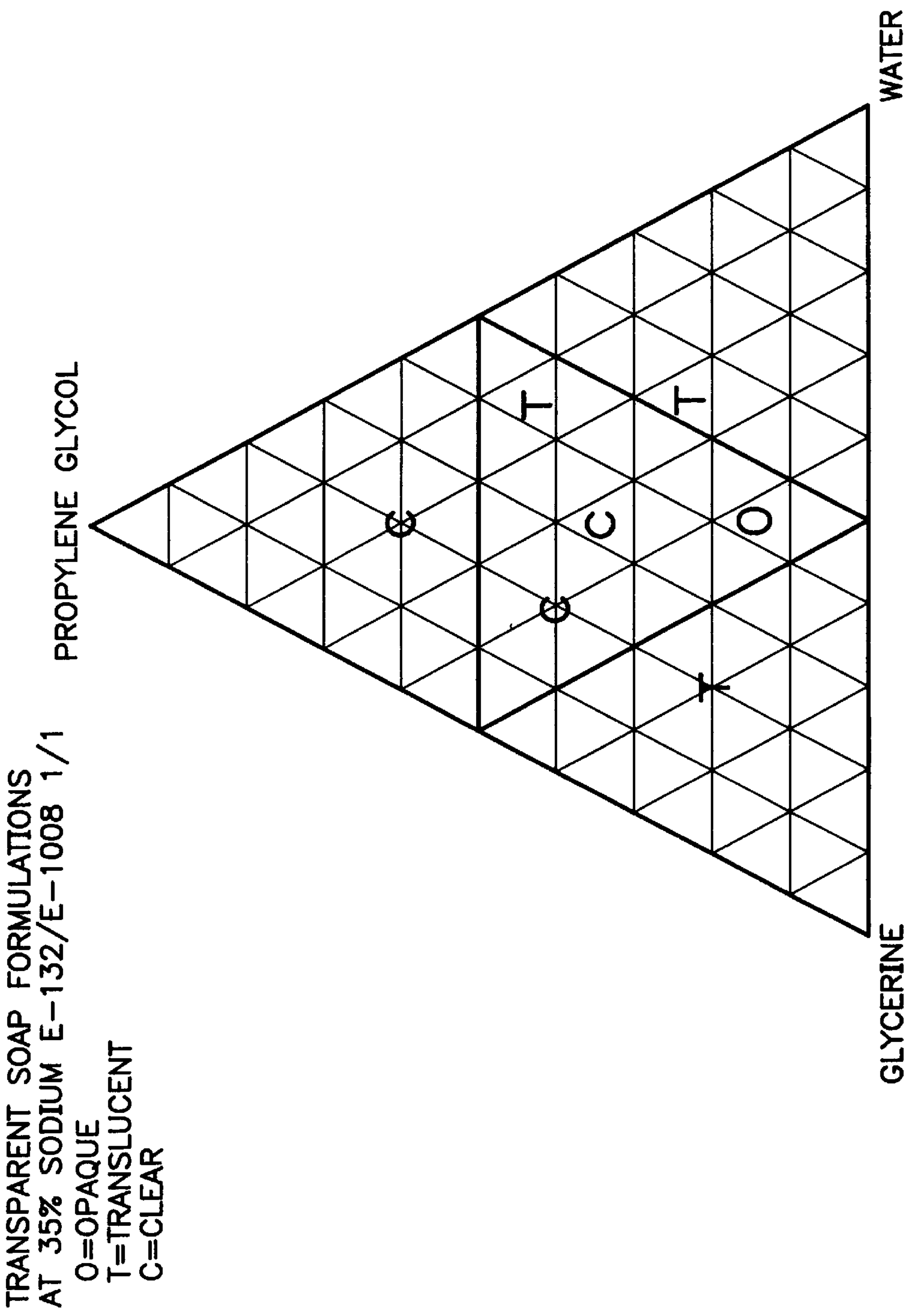
FIG. 2 is a representative three component phase diagram for a transparent soap bar which shows the transparent region for a relative amounts of water, 1,2-propylene glycol and glycerine and which contains one or more additives according to the invention which enlarge the transparent area thereby permitting greater latitude in formulating soap bars that are transparent.

It has been discovered that the incorporation of one or more additives selected from the group consisting of: (a) an aliphatic or aromatic dicarboxylic acid having from 2 to 36 carbon atoms; (b) an a branched aliphatic monocarboxylic acid having from 4 to 22 carbon atoms; (c) the product of the reaction of a monocarboxylic acid, a dicarboxylic acid, and a polyol into transparent soap bar formulations according to the invention permits the use of increased amounts of water thereby decreasing the amounts of the more costly polyols, such as 1,2-propylene glycol and glycerine, alkanolamines and saturated fatty acids. The incorporation of one or more of such additives results in a larger area of transparency on a three component phase diagram as shown by comparing FIGS. 1 and 2. FIG. 1 is a representative three component phase diagram for a transparent soap bar which shows the transparent region for a relative amounts of water, 1,2-propylene glycol and glycerin. FIG. 2 is a generic representation of the effect of the addition of one of the additives according to the invention. The transparency region is larger and shifted toward greater amounts of water and lesser amounts of propylene glycol in FIG. 2 because of the presence of the additive. The larger transparency region shows that there is a greater degree of freedom in choosing the relative amounts of water, 1,2-propylene glycol and glycerin while remaining in the transparent area. Preferably, the soap bars according to the invention will typically contain an amount of one or more additives as set forth above in an amount effective to inhibit the formation of hazy domains in the transparent soap bars and/or enlarge the transparent area in a three component phase diagram such as shown in FIGS. 1 and 2. The effective amount for any particular soap bar formulation will depend upon the composition of the soap bar and will be readily ascertainable by the person of ordinary skill in the art.

The first type of additive as set forth above is an aliphatic or aromatic dicarboxylic acid having from 2 to 36 carbon atoms. Such an acid can be any branched aliphatic dicarboxylic acid or aromatic dicarboxylic acid having one or more fused benzene rings and having from 2 to 36 carbon atoms. Preferred dicarboxylic acids are typical commercial dimer acids produced by the polymerization of C-18 fatty acids such as EMPOL® 1008 Dimer Acid, EMPOL® 1014 Dimer Acid, and EMPOL® 1022 Dimer Acid.

The second type of additive according to the invention is an aliphatic monocarboxylic acid having one or more branches in the carbon chain of the acyl group and having from 4 to 22 carbon atoms. Such branched carboxylic acids can be single compounds or, more typically, commercial branched fatty acids which are complex mixtures of isomers, primarily methyl-branched fatty acids. Preferred branched fatty acids are typical commercial isostearic acids such as EMERSOL® 871 Isostearic Acid and EMERSOL® 875 Isostearic Acid, trademark products of Henkel Corporation, Emery Group, Cincinnati, Ohio.

The third type of such additive is the product of the reaction of a monocarboxylic acid, a dicarboxylic acid, and a polyol. Preferably, the additive is the reaction product of glycerine, a fatty acid, and dimer acid. Most preferably, 30 parts by weight of stearic acid, 20 parts by weight of a C-36 dimer acid, and 50 parts by weight of glycerine are reacted at 286° C. for a period of time sufficient to drop the acid number into the 20 to 10 range.

The following examples are meant to illustrate but not limit the invention.

EXAMPLE 1

Soap bars A and B, the composition of which is given in the table below, were made by the following procedure. The NaOH was dissolved in water and added to an aqueous solution comprised of triethanolamine, alkyl polyglycoside, and glycerine. The combined solution was heated to and maintained at 70° C. The fatty acids were melted, heated to 70° C., and added to the combined aqueous solution. The combined soap-aqueous solution mixture was maintained at a temperature of less than 85° C. and stirred until homogeneous at which point it was deaerated, the foam skimmed off, and the poured into molds and cooled. The incorporation of alkyl polyglycosides enables the water/free triethanolamine weight ratio to be greater than 1.0. Both bars were transparent. All amounts are in weight percent.

| Bar | TEA[1] | Water | E-918[2] | APG ® 225 | Fatty acid[3] | NaOH |
|---|---|---|---|---|---|---|
| A | 19 | 13.3 | 3.9 | 20.1 | 38.4 | 5.75 |
| B | 15.7 | 8.6 | 11.8 | 20.1 | 38.4 | 5.8 |

1-free triethanolamine
2-EMERY ® 918 - 99.7% glycerin
3-Amount of 40% by wgt. EMERY ® 625 Partially Hydrogenated Coconut Fatty Acid + 60% by wgt. EMERSOL ® 132 Stearic Acid

What is claimed is:

1. A transparent soap bar having improved lathering and foaming characteristics comprising: (1) an alkanolamine; (2) an alkyl polyglycoside of the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6: (3) a polyol; (4) a fatty acid having a degree of neutralization of at least about 70%, and; (5) water; wherein the water to free alkanolamine weight ratio is greater than 1.0 and wherein the ratio of the weight of polyol to the sum of the weights of free alkanolamine+alkyl polyglycoside+polyol+water is less than about 0.4.

2. The soap bar of claim 1 wherein $R_1$ is an alkyl radical having from about 8 to about 10 carbon atoms and a is about 1.5 to about 1.8.

3. The soap bar of claim 1 wherein $R_1$ is an alkyl radical having from about 12 to about 16 carbon atoms and a is about 1.5 to about 1.8.

4. The soap bar of claim 1 wherein said alkanolamine is monoethanolamine, diethanolamine, and triethanolamine.

5. The soap bar of claim 4 wherein said alkanolamine is triethanolamine.

6. The soap bar of claim 1 wherein the amount of said alkanolamine is from about 25 to about 76 wgt. %.

7. The soap bar of claim 6 wherein said amount is from about 21 to about 48 wgt. %.

8. The soap bar of claim 1 wherein said polyol is 1,2-propylene glycol, glycerine, polyglycerol, and sorbitol.

9. The soap bar of claim 8 wherein said polyol is glycerine.

10. The soap bar of claim 1 wherein the amount of said polyol is at least 1.5 wgt. %.

11. The soap bar of claim 1 wherein said fatty acid is a saturated or unsaturated, branched or linear fatty acid having from 8 to 36 carbon atoms or a mixture of such acids.

12. The soap bar of claim 11 wherein said fatty acid is a mixture of fatty acids comprised of 60% by weight of stearic acid and 40% by weight of a partially hydrogenated coconut fatty acid.

13. The soap bar of claim 1 wherein the amount of said fatty acid is from about 20 to about 60 wgt. %.

14. The soap bar of claim 1 wherein said amount is from about 30 to about 55 wgt. %.

15. The soap bar of claim 1 further comprising an aliphatic or aromatic dicarboxylic acid having from 2 to 36 carbon atoms.

16. The soap bar of claim 15 wherein said dicarboxylic acid is a C-36 dimer acid.

17. The soap bar of claim 1 further comprising an a branched aliphatic monocarboxylic acid having from 4 to 22 carbon atoms.

18. The soap bar of claim 17 wherein said branched aliphatic monocarboxylic acid is isostearic acid.

19. The soap bar of claim 1 further comprising an additive which is comprised of the product of the reaction of a monocarboxylic acid, a dicarboxylic acid, and a polyol.

20. The soap bar of claim 19 wherein said additive is the product of the reaction of stearic acid, C-36 dimer acid, and glycerine.

21. The soap bar of claim 20 wherein the weight ratio of said stearic acid to said C-36 dimer acid to said glycerine is from about 0.1 to about 2 wgt. %.

22. The soap bar of claim 1 wherein said degree of neutralization is from about 70% to 110%.

23. The soap bar of claim 22 wherein said degree of neutralization is from about 85 to about 95%.

24. The soap bar of claim 1 wherein the total amount of carboxylic acids is from about 18 to about 60 wgt. %.

25. The soap bar of claim 24 wherein said total is from about 23 to about 38 wgt. %.

26. A transparent soap bar having improved lathering and foaming characteristics comprising: (1) triethanolamine; (2) an alkyl polyglycoside of the formula I $$R_1(R_2O)_b(Z)_a \quad (I)$$

wherein $R_1$ is a monovalent organic radical having from about 6 to about 30 carbon atoms; $R_2$ is divalent alkylene radical having from 2 to 4 carbon atoms; Z is a saccharide residue having 6 carbon atoms; b is zero; a is a number having a value from 1 to about 1.8; (3) glycerine; (4) a mixture of fatty acids comprised of (i) about 60% by weight of a stearic acid composition comprising about 2.5% myristic acid, about 1% pentadecanoic acid, about 50% palmitic acid, about 1.5% margaric acid, and about 45.5% stearic acid and: (ii) about 40% by weight of a partially hydrogenated coconut fatty acid composition comprising about 49% lauric acid, 19% myristic acid, 9% palmitic acid, 7% stearic acid, 7% caprylic acid, 6% capric acid, and 3% oleic acid wherein said mixture at least about 70% neutralized, and; (5) water; wherein the water to free alkanolamine weight ratio is greater than 1.0 and wherein the ratio of the weight of glycerine to the sum of the weights of triethanolamine+alkyl polyglycoside+glycerine+water is less than about 0.4.

27. The soap bar of claim 26 wherein $R_1$ is an alkyl radical having from about 8 to about 10 carbon atoms and a is about 1.5 to about 1.8.

28. The soap bar of claim 27 wherein $R_1$ is an alkyl radical having from about 12 to about 16 carbon atoms and a is about 1.5 to about 1.8.

29. The soap bar of claim 27 wherein the amount of triethanolamine is from about 25 to about 76 wgt. %.

30. The soap bar of claim 29 wherein said amount is from about 21 to about 48 wgt. %.

31. The soap bar of claim 27 wherein the amount of glycerine is greater than about 1.5 wgt. %.

32. The soap bar of claim 27 further comprising an aliphatic or aromatic dicarboxylic acid having from 2 to 36 carbon atoms.

33. The soap bar of claim 32 wherein said dicarboxylic acid is a C-36 dimer acid.

34. The soap bar of claim 27 further comprising an a branched aliphatic monocarboxylic acid having from 4 to 22 carbon atoms.

35. The soap bar of claim 34 wherein said branched aliphatic monocarboxylic acid is isostearic acid.

36. The soap bar of claim 27 further comprising an additive which is comprised of the product of the reaction of a monocarboxylic acid, a dicarboxylic acid, and a polyol.

37. The soap bar of claim 36 wherein said additive the product of the reaction of stearic acid, C-36 dimer acid, and glycerine.

38. The soap bar of claim 37 wherein the weight ratio of said stearic acid to said C-36 dimer acid to said glycerine is from about 0.1 to about 2 wgt. %.

39. The soap bar of claim 27 wherein said degree of neutralization is from about 70% to 110%.

40. The soap bar of claim 27 wherein said degree of neutralization is from about 85 to about 95%.

41. The soap bar of claim 27 wherein the total amount of carboxylic acids is from about 18 to about 60 wgt. %.

42. The soap bar of claim 41 wherein said total is from about 20 to about 45 wgt. %.

43. A method of producing a transparent soap bar having a reduced number of hazy domains and wherein said bar is comprised of: (1) an alkanolamine; (2) an alkyl polyglycoside of the formula I $$R_1(R_2O)_b(Z)_a \qquad (I)$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6: (3) a polyol; (4) a fatty acid having a degree of neutralization of at least about 70%, and; (5) water; wherein the water to free alkanolamine weight ratio is greater than 1.0 and wherein the ratio of the weight of the polyol to the sum of the weights of alkanolamine+alkyl polyglycoside+polyol+water is less than about 0.4 which comprises adding an amount of an additive selected from the group consisting of: (a) an aliphatic or aromatic dicarboxylic acid having from 2 to 36 carbon atoms; (b) a branched aliphatic monocarboxylic acid having from 4 to 22 carbon atoms; (c) the product of the reaction of a monocarboxylic acid, a dicarboxylic acid, and a polyol; and combinations thereof wherein said additive is added in amount effective to inhibit the formation of hazy domains in said transparent soap bar.

44. The process of claim 43 wherein said branched aliphatic monocarboxylic acid is isostearic acid.

45. The process of claim 43 wherein said additive is the product of the reaction of a monocarboxylic acid, a dicarboxylic acid, and a polyol.

46. The process of claim 45 wherein said monocarboxylic acid is stearic acid, said dicarboxylic acid is a C-36 dimer acid, and said polyol is glycerine.

47. The process of claim 46 wherein the weight ratio of said stearic acid to said C-36 dimer acid to said glycerine is from about 0.1 to about 2 wgt. %.

48. The process of claim 43 wherein said additive is an aliphatic or aromatic dicarboxylic acid having from 2 to 36 carbon atoms.

49. The process of claim 48 wherein said dicarboxylic acid is a C-36 dimer acid.

50. The process of claim 43 wherein the degree of neutralization of said fatty acid of component (4) is from about 70% to 110%.

51. The process of claim 50 wherein said degree of neutralization is from about 85 to about 95%.

52. The soap bar of claim 43 wherein the total amount of carboxylic acids is from about 18 to about 60 wgt. %.

* * * * *